US006833449B1

(12) United States Patent
Barton et al.

(10) Patent No.: US 6,833,449 B1
(45) Date of Patent: Dec. 21, 2004

(54) EXPRESSION OF THE TOXIC PORTION OF CRY1A IN PLANTS

(75) Inventors: Kenneth A. Barton, Middleton, WI (US); Michael J. Miller, Cross Plains, WI (US)

(73) Assignee: Monsanto Technology LLC, St. Louis, MO (US)

( * ) Notice: Subject to any disclaimer, the term of this patent is extended or adjusted under 35 U.S.C. 154(b) by 112 days.

(21) Appl. No.: 10/394,548

(22) Filed: Mar. 21, 2003

Related U.S. Application Data

(63) Continuation of application No. 07/827,906, filed on Jan. 30, 1992, which is a continuation of application No. 07/390,561, filed on Aug. 7, 1989, now abandoned.

(51) Int. Cl.[7] ................................................ C12N 15/32

(52) U.S. Cl. .................................................... 536/23.71

(58) Field of Search ....................................... 536/23.71

(56) References Cited

U.S. PATENT DOCUMENTS

| | | | | |
|---|---|---|---|---|
| 4,859,596 A | | 8/1989 | Hollenberg et al. | |
| 5,380,831 A | | 1/1995 | Adang et al. | |
| 5,496,732 A | | 3/1996 | Smigocki et al. | |
| 5,500,365 A | * | 3/1996 | Fischhoff et al. | 435/418 |
| 5,567,600 A | * | 10/1996 | Adang et al. | 536/23.71 |

FOREIGN PATENT DOCUMENTS

| | | |
|---|---|---|
| AU | B-36568/89 | 12/1989 |
| AU | B-46881/89 | 6/1990 |
| EP | 0 126 546 | 11/1984 |
| EP | 0 140 556 | 5/1985 |
| EP | 0 159 884 | 10/1985 |
| EP | 0 275 957 | 7/1988 |
| EP | 0 318 143 | 5/1989 |
| EP | 0 359 472 | 3/1990 |

OTHER PUBLICATIONS

Adami et al., Adenovirus mRNA processing—in a regulated manner a splice site choice dominates over selection of a poly A site located in an intron, Abstract presented at meeting on RNA processing, May 11–15, 1988, *Cold Spring Harbor,* p. 26.

Adang et al, Expression of a *Bacillus thuringiensis* insecticidal crystal protein gene in Tobacco plants, *Molecular Strategies for Crop Protection, 48*:345–353 (1987).

Adang et al., Characterized full–length and truncated plasmid clones of the crystal protein of *Bacillus thuringiensis* subsp. *kurstaki* HD–73 and their toxicity to *Manduca sexta, Gene 36*:289–300 (1985).

Barton et al., *Bacillus thuringiensis* delta–endotoxin expressed in transgenic nicotiana tabacum provides resistance to lepidotperan insects, *Plant Physiology 85*:1103–1109 (1987).

Brady et al., Competition between Splicing and Polyadenylation determines which adenovirus region E3 mRNAs are synthesized, Abstract presented at meeting on RNA processing, May 11–15, 1988, *Cold Spring Harbor,* p. 224.

Brown, A Catalogue of splice junction and putative branch point sequences from plant introns, *Nucl. Acids Res. 14*:9549–9559 (1986).

Conway et al., Identification of Bases and Phosphates of SV40 Late Pre–mRNAs that are Required for 3' end Formation in Vitro, Abstract presented at meeting on RNA Processing May 11–15, 1988, *Cold Spring Harbor,* p. 40.

Daar et al., Premature Translation Termination Mediates Mammalian mRNA Degradation, Abstract presented at meeting on RNA processing, May 11–15, 1988, *Cold Spring Harbor,* p. 45.

Dalbadie–McFarland et al., Oligonucleotide Directed Mutagenesis as a General and Powerful Method for Studies of Protein Function, *Proc. Natl. Acad. Sci. USA 79*:6409–6413 (1982).

Dean et al., mRNA Transcripts of Several Plant Genes are Polyadenylated at Multiple Sites in Vivo, *Nucl. Acid. Res. 14*:2229–2240 (1986).

Dedrick et al., Purified RNA polymerase II recognizes specific termination sites during transcription in vitro, *J. Biol. Chem. 262*:9098–9108 (1987).

Donovan et al., Amino acid sequence and entomocidal activity of the P2 Crystal protein, *J. Biol. Chem. 263*:561–567 (1988).

Fischhoff et al., Insect Tolerant Transgenic Tomato Plants, *Biotechnology 5*:807–813 (1987).

Gallego et al., Mutually Exclusive Splicing of Myosin Light Chain (MLC) 1/3 Transcripts is Cis Regulated: Hierarchy among donor and acceptor splice site pairs, Abstract presented at meeting on RNA processing, May 11–15, 1988, *Cold Spring Harbor,* p. 61.

Genovese et al., Alterations in Immunoglobulin mRNA stability during B cell development, Abstract presented at meeting on RNA processing, May 11–15, 1988, *Cold Spring Harbor,* p. 62.

Gil et al., A sequence downstream of AAUAAA is required for rabbit β–globin m RNA 3'–end formation, *Nature* 312:473–474 (1984).

Goodall et al., Specificity of Nuclear pre–RNA splicing in Plants, Abstract presented at meeting on RNA processing, May 11–15, 1988, *Cold Spring Harbor,* p. 63.

Grantham et al., Patterns in codon usage of differen tkinds of species, *Oxford Surveys in Evol. Biol. 3*:48–81 (1986).

(List continued on next page.)

*Primary Examiner*—Anne Kubelik
(74) *Attorney, Agent, or Firm*—Timothy K. Ball

(57) ABSTRACT

Disclosed is a method for improving the expression of Cry1A in plants that makes use of codons preferentially used in native plant genes. The coding sequence of the gene for the *Bacillus thuringiensis* delta endotoxin Cry1A crystal protein was analyzed and found to have codons not preferred by plants. By constructing a synthetic protein coding sequence that uses codons which are preferred in plant genes, expression of the protein in plant cells was improved.

3 Claims, 6 Drawing Sheets

OTHER PUBLICATIONS

Hampson et al., Alternative Processing of Bovine Growth Hormone Precursor mRNA is strongly Influenced by Sequences within the downstream Exon, Abstract presented at meeting on RNA processing, May 11–15, 1988, *Cold Spring Harbor,* p. 68.

Hanley et al., Plant Intron Sequences: Evidence for Distinct Groups of Introns, *Nucl. Acids Res. 16*:7159–7176 (1988).

Helfman et al., Studies of Alternative RNA Splicing of Tropomyosin Pre–mRNAs in Vitro, Abstract presented at meeting on RNA processing, May 11–15, 1988, *Cold Spring Harbor,* p. 219.

Hoekma et al., Codon Replacement in the PGK1 Gene of *Saccharomyces cerevisiae*: Experimental Approach to Study the Role of Biased Codon Usage in Gene Expression, *Molecular and Cellular Biology 7*:2914–2924 (1987).

Hofte et al., Insecticidal Crystal Proteins of *Bacillus thuringiensis, Microbiological Reviews 52*(*2*):242–255 (1989).

Hofte et al., Nucleotide sequence of a gene encoding an insecticidal protein of *Bacillus thuringiensis* var. *tenebrionis* toxic against Coleoptera, *Nucl. Acids Res. 15*:7183 (1987).

Honee et al., Nucleotide Sequence of Crystal Protein Gene Isolated From *B. thuringiensis* Subspecies, *entomocidus* 60.5 Coding for a Toxin Highly Active Against Spodoptera Species, *Nucleic Acids Research 16*:6240 (1988).

Honigman et al., Cloning an dexpression of the lepidopteran toxin produced by *Bacillus thuringiensis* var. *thuringiensis* in *Escherichia coli, Gene 42*:69–77 (1986).

Kessler et al., A novel transcription elongation block is active within the late leader sequences of SV40, Abstract presented at meeting on RNA processing, May 11–15, 1988, *Cold Spring Harbor*, p. 85.

Kozak, Influences of mRNA Secondary Structure on Initiation by Eukaryotic Ribosomes, *Biochemistry, Proc. Natl. Acad. Sci. USA 83*:2850–2854 (1986).

Lim et al., Tissue Specificity of mRNA Degradation, Abstract presented at meeting on RNA processing, May 11–15, 1988, *Cold Spring Harbor,* p. 128.

Marzluff et al., Intervening Sequences Interfere with Formation of 3' Ends of Histone mRNAs, Abstract presented at meeting on RNA processing, May 11–15, 1988, *Cold Spring Harbor*, p. 244.

McDevitt et al., Requirement of a Downstream Sequence for Generation of Poly(A) addition site, *Cell 37*:993–999 (1984).

Murray et al., Codon usage in plant genes, *Nucleic Acids Research 17*:477–498 (1989).

Pandley et al, Processing and Stability of Transcripts from Chimeric Histone–Globin Genes, Abstract presented at meeting in RNA Processing May 13–17, 1987, *Cold Spring Harbor*, p. 133.

Potryktus, Gene transfer to Cereals: An Assessment, *Biotechnology 8*:535–542 (1990).

Proudfoot et al., Termination of Transcription and 3' end processing in Eukaryotic Genes transcribed by RNA polymerase II: The signals involved and their role in gene regulation, Abstract presented at meeting on RNA Processing May 13–17, 1987, *Cold Spring Harbor,* p. 17.

Reines et al., Identification of Intrinsic Termination Sites in Vitro for RNA Polymerase II Within Eukaryotic Gene Sequences, *J. Mol. Biol. 196*:299–312 (1987).

Sadofsky et al., Sequences on the 3' side of Hexanucleotide AAUAAA Affect efficiency of Cleavage at the Polyadenylation site, *Mol. & Cell Biol. 4*:1460–1468 (1984).

Schnepf et al., The Amino Acid Sequence of a Crystal Protein from *Bacillus thuringiensis* Deduced from the DNA Base Sequence, *Journal of Biological Chemistry 260*:6264–6272 (1985).

Seeburg et al., Characterization of cDNA for precursor of human luteinizing hormone releasing hormone, *Nature 311*:666–668 (1984).

Shaw et al., Conserved AU Sequence from the 3' Untranslated Region of GN–CSF and mRNA Mediates Selective mRNA Degradation, *Cell 46*:659–667 (1986).

Shaw et al., Characterization of AU Sequences Functioning as mRNA Destabilizers, Abstract presented at meeting on RAN processing, May 13–17, 1987, *Cold Spring Harbor,* p. 220.

Smith et al., Molecular Cloning of Potato Leaf Roll Virus Complementary DNA, *Biol. Abstr. Phytopathology 87*:AB9696 (1989).

Smith et al., Colecular Cloning of Potato Leaf Roll Virus Complementary DNA, *Phytopathology78*:1060–1066 (1988).

Tsurushita and Korn, Regulation of Differential Processing of Mouse Immunogolubin My Heavy–Chain mRNA, Abstract Presented at Meeting on RNA Processing May 13–17, 1987, *Cold Spring Harbor,* p. 215.

Vaeck et al., Transgenic plants protected from insect attack, *Nature 328*:33–37 (1987).

Wickens et al., Cleavage and Polyadenylation of SV40 Late Pre–mRNAs in vitro, Abstract presented at meeting on RNA Processing, May 13–17, 1987, *Cold Spring Harbor,* p. 9.

Wiebauer et al., Nuclear Pre–mRNA processing in Plants: Distinct Modes of 3' splice site selection in plants and animals, *Mol. & Cell. Biol. 8*:2042–2051 (1988).

Barker et al., Nucleotide sequence of the T–DNA region from the *Agrobacterium tumefaciens* octopine Ti plasmid pTi15955, *Plant Mol. Biol.* 2:335–350 (1983).

Barton et al., Prospects in Plant Genetic Engineering, *Science 219*:671–675 (1983).

Barton et al., Regeneration of Intact Tobacco Plants Containing Full Length Copies of Genetically Engineered T–DNA and Transmission of T–DNA to R1 Progeny, *Cell 32*:1033–1043 (1983).

Bauer et al., *Chimie der Pflanz,* pp. 289–295 (1981).

Barton et al., Production of *Bacillis thuringiensis* Insecticidal Proteins in Plants, *Transgenic Plants,* pp. 297–315 (1993).

Borlaug, Contributions of Conventional Plant Breeding to Food Production, *Science 219*:689–693 (1983).

Callis et al., Introns increase gene expression in cultured maize cells, *Genes and Development 1*:1183–1200 (1987).

Caplan et al., Introduction of Genetic Material into Plant Cells, *Science* 222:815–821 (1983).

Chilton et al., Tailoring the Agrobacterium Ti Plasmid as a Vector for Plant Genetic Engineering, *Stadler Symp 13*:39–51 (1981).

Chilton, A Vector for Introducing New Genes into Plants, *Scientific American 249*:50–59 (1983).

Church et al., Genomic sequencing, *PNAS, USA 18*:1991–1995 (1984).

Dandekar et al., Low levels of expression of wild type *Bacillus thuringiensis* var. *kurstaki cryIA* (c) sequences, in transgenic walnut somatic embryos, *Plant Science 96*: 151–162 (1994).

De Cleene et al., The Host Range of Crown Gall, *Botanical Review 42*:389–466 (1976).

Foard et al., Engineering of Crop Plants with Resistance to Herbivores and Pathogens: An Approach Using Primary Gene Products, *Proc. ARCO Solar– UCLA Symp.*, pp. 223–233 (1983).

Fraley et al., Use of a Chimeric Gene to Confer Antibiotic Resistance to Plant Cells, *15th Miami Winter Symposium,* pp. 211–221 (1983).

Fraley et al., Expression of bacterial genes in plant cells, *PNAS USA 80*:4803–4807 (1983).

Gelvin et al., Use of a Tr T–DNA promoter to express genes in palnts and bacteria, *Mol., Gen. Genet. 199*:240–248 (1985).

Goldsborough et al., Expression of maize zein genes in transformed sunflower cells, *Mol. Gen. Genet. 202*:374–381 (1986).

Green et al., Wound–Induced Proteinase Inhibitor in Plant Leaves: A Possible Defense Mechanism against Insects, *Science 175*:776–777 (1972).

Grimsley et al., Agrobacterium–mediated delivery of infectious maize streak virus into maize plants, *Nature 325*:177–179 (1987).

Held et al., Cloning an dlocalization of the lepidopteran protoxin gene of *Bacillus thuringiensis* subsp. *kurstaki, PNAS USA 79*:6065–6069 (1982).

Herrera–Estrella et al., Expression of chimaeric genes transferred into plant cell susing a Ti–plasmid–derived vector, *Nature 303*:309–313 (1983).

Hinchee et al., Production of Transgenic Soybean Plants Using Agrobacterium–Mediated DNA Transfer, *Biotechnology 6*:915–922 (1988).

Hooykaas et al., *Plant Mol. Biol. 11*:791–794 (1988).

Horsch et al., A Simple and General Method for Transferring Genes into Plants, Science 277:1229–1231 (1985).

Janssen et al., *Plant Mol. Biol. 14*:61–72 (1989).

Janzen et al., Insecticidal Action of the Phytohemagglutinin in Black Bears on a Bruchid Beetle, *Science 192*:795–796 (1976).

Keith et al., Monocot and dicot pre–mRNAs are processed with different efficiencies in transgenic tobacco, *EMBO J. 5*:2419–2425 (1986).

Kemp, Agrobacterium–Mediated Transfer of Foreign Genes into Plants, *Genetic Enginering,* pp. 215–228 (1983).

Klier et al., Cloning an dexpressionof the crystal protein genes from *Bacillus turingiensis* strain *berliner* 1715, *EMBO J. 1*:791–799 (1982).

Korber et al., T–DNA gene 5 of Agrobacterium modulates auxin response by autoregulated synthesis of a growth hormone antagonist in plants, *EMBO J. 10*:3983–3991 (1991).

Kronstad et al., Diversity of Locations for *Bacillus thuringiensis* Crystal Protein Genes, *J. Bacteriol. 154*:419–428 (1983).

Ledeboer, Advances in Gene Technology For Plants and Animals, *Biotechnology,* pp. 169–171 (1983).

Leemans et al., Genetic identification of functions of TL–DNA transcripts in octopine crown galls, *EMBO J. 1*:147–152 (1982).

Luthy et al., The Entomocidal Toxins of *Bacillus thuringiensis, Pharmac. Ther. 13*:257–283 (1981).

MacIntosh et al., Specificity and Efficacy of Purified *Bacillus thuringiensis* Proteins against Agronomically Important Insects, *J. Invertebrate Path. 56*:258–266 (1990).

Marx, Ti Plasmids as Gene Carriers, *Science 216*:1305 (1982).

Maugh, Exploring Plant Resistance to Insects, *Science 216*:722–723 (1982).

Miller et al., Bacterial, Viral, and Fungal Insecticides, *Science* 715–721 (1983).

Murray et al., Analysis of unstable RNA transcripts of insecticidal crystal protein genes of *Bacillus thuringiensis* in transgenic plants and electroporated protoplasts, *Plant Mol. Biol. 16*:1035–1050 (1991).

Osborn et al., Insecticidal Activity and Lectin Homology of Arcelin Seed Protein, *Science 240*:207–210 (1988).

Peerbolte et al., *Plant Mol. Biol. 7*:265–284 (1986).

Rogan et al., Enzyme–Linked Immunosorbent Assay for Quantitation of Neomycin Phosphotransferase II in Genetically Modified Cotton Tissue Extracts, *J. Agric. Food Chem. 40*:1453–1458 (1992).

Saghai–Maroof et al., Ribosomal DNA spacer–length polymorphisms in barley: Mendelian inheritance, chromosomal location, and population dynamics, *Proc. Natl. Acad. Sci.* USA, 81:8014–8018 (1984).

Schell et al., The Ti Plasmids as Natural and as Practical Gene Vectors for Plants, *Biotechnology* 175–180 (1983).

Schell et al., Ti Plasmids as Experimental Gene Vectors for Plants, 15th *Miami Winter Symposium,* pps 192–209 (1983).

Schesser et al., Bioassay for Homogeneous Parasporal Crystal of *Bacillus thuringiensis* Using the Tobacco Hornworm, *Manduca sexta, Appl. Env. Microbiol.* pp878–880 (1977).

Schnepf et al., Delineation of a Toxin–encoding Segment of a *Bacillus thuringiensis* Crystal Protein Gene, *J. Biol. Chem. 260*:6273–6278 (1985).

Schnepf et al, Cloning And expression of the *Bacillus thuringiensis* crystal protein gene in *Escherichia coli, PNAS, USA 78*:2893–2897 (1981).

Smigocki et al., Cytokinin–mediated insect resistance in Nicotiana plants transformed with the ipt gene, *Plant Mol. Biol. 23*:325–335 (1993).

Spanier et al., A functional analysis of T–DNA gene 6b: The fine tuning of cytokinin effects on shoot development, *Mol. Gen. Genet. 219*:209–216 (1989).

Thurston, Toxicity of Trichome Exudates of *Nicotiana* and *Petunia* Species to Tobacco Hornworm Larvae, *J. Econom. Enc 63*:272–274 (1970).

Tinland et al., *Agrobacterium tumefaciens* T–DNA gene 6b stimulates rol–induced root formation, permits growth at high auxin concentrations and increase root size, *Mol. Gen. Genet. 223*:1–10 (1990).

Trolinder et al., Somatic embryogenesis and plant regeneration in cotton *Gossypium hirsutum L.*), *Plant Cell Reports 6*:231–234 (1987).

Vancanneyt et al., Construction of an intron–containing marker gene: Splicing of the intron in transgenic plants and its use in monitoring early events in Agrobacterium–mediated plant transformation, *Mol. Gen. Genet. 220*:245–250 (1990).

Wendel, New World tetraploid cottons contain Old World cytoplasm, *PNAS, USA 86*:4132–4136 (1989).

Whitely et al., Cloning the Crystal Protein Gene of *B. thuringiensis* in *E. coli, Molecular Cloning* and *Gene Regulation in Bacilli,* pp. 131–144 (1982).

Wong et al., Transcriptional and Translational Start Sites for the *Bacillus thuringiensis* Crystal Protein Gene, *J. Biol. Chem. 258*:1960–1967 (1983).

Wong et al., Differential Accumulation of Proteinase Inhibitor I in Normal and Crown Gall Tissues of Tobacco, Tomato, and Potato, *Plant Physiol. 57*:214–217 (1976).

* cited by examiner

CODON USAGE IN PLANTS FREQUENCY TABLE

| AmAcid | Codon | Number | /1000 | Fraction |
|---|---|---|---|---|
| Gly | GGG | 160.00 | 10.23 | 0.12 |
| Gly | GGA | 323.00 | 20.66 | 0.25 |
| Gly | GGT | 355.00 | 22.70 | 0.28 |
| Gly | GGC | 445.00 | 28.46 | 0.35 |
| Glu | GAG | 668.00 | 42.72 | 0.71 |
| Glu | GAA | 278.00 | 17.78 | 0.29 |
| Asp | GAT | 340.00 | 21.74 | 0.45 |
| Asp | GAC | 422.00 | 26.99 | 0.55 |
| Val | GTG | 390.00 | 24.94 | 0.33 |
| Val | GTA | 69.00 | 4.41 | 0.06 |
| Val | GTT | 369.00 | 23.60 | 0.32 |
| Val | GTC | 340.00 | 21.74 | 0.29 |
| Ala | GCG | 214.00 | 13.69 | 0.16 |
| Ala | GCA | 213.00 | 13.62 | 0.15 |
| Ala | GCT | 460.00 | 29.42 | 0.33 |
| Ala | GCC | 490.00 | 31.34 | 0.36 |
| Lys | AAG | 726.00 | 46.43 | 0.81 |
| Lys | AAA | 168.00 | 10.74 | 0.19 |
| Asn | AAT | 203.00 | 12.98 | 0.32 |
| Asn | AAC | 430.00 | 27.50 | 0.68 |
| Met | ATG | 376.00 | 24.05 | 1.00 |
| Ile | ATA | 69.00 | 4.41 | 0.08 |
| Ile | ATT | 320.00 | 20.46 | 0.39 |
| Ile | ATC | 434.00 | 27.75 | 0.53 |
| Thr | ACG | 104.00 | 6.65 | 0.13 |
| Thr | ACA | 119.00 | 7.61 | 0.15 |
| Thr | ACT | 232.00 | 14.84 | 0.29 |
| Thr | ACC | 336.00 | 21.49 | 0.42 |
| Trp | TGG | 232.00 | 14.84 | 1.00 |
| Cys | TGT | 81.00 | 5.18 | 0.29 |
| Cys | TGC | 200.00 | 12.79 | 0.71 |

| AmAcid | Codon | Number | /1000 | Fraction |
|---|---|---|---|---|
| Tyr | TAT | 122.00 | 7.80 | 0.24 |
| Tyr | TAC | 377.00 | 24.11 | 0.76 |
| Phe | TTT | 192.00 | 12.28 | 0.28 |
| Phe | TTC | 493.00 | 31.53 | 0.72 |
| Ser | AGT | 97.00 | 6.20 | 0.09 |
| Ser | AGC | 280.00 | 17.91 | 0.26 |
| Ser | TCG | 111.00 | 7.10 | 0.10 |
| Ser | TCA | 147.00 | 9.40 | 0.14 |
| Ser | TCT | 179.00 | 11.45 | 0.17 |
| Ser | TCC | 250.00 | 15.99 | 0.23 |
| Arg | AGG | 174.00 | 11.13 | 0.24 |
| Arg | AGA | 119.00 | 7.61 | 0.17 |
| Arg | CGG | 57.00 | 3.65 | 0.08 |
| Arg | CGA | 35.00 | 2.24 | 0.05 |
| Arg | CGT | 145.00 | 9.27 | 0.20 |
| Arg | CGC | 189.00 | 12.09 | 0.26 |
| Gln | CAG | 325.00 | 20.78 | 0.64 |
| Gln | CAA | 186.00 | 11.89 | 0.36 |
| His | CAT | 151.00 | 9.66 | 0.43 |
| His | CAC | 197.00 | 12.60 | 0.57 |
| Leu | TTG | 232.00 | 14.84 | 0.18 |
| Leu | TTA | 36.00 | 2.30 | 0.03 |
| Leu | CTG | 306.00 | 19.57 | 0.24 |
| Leu | CTA | 65.00 | 4.16 | 0.05 |
| Leu | CTT | 279.00 | 17.84 | 0.22 |
| Leu | CTC | 364.00 | 23.28 | 0.28 |
| Pro | CCG | 222.00 | 14.20 | 0.24 |
| Pro | CCA | 264.00 | 16.88 | 0.29 |
| Pro | CCT | 229.00 | 14.64 | 0.25 |
| Pro | CCC | 200.00 | 12.79 | 0.22 |
| End | TAG | 11.00 | 0.70 | 0.23 |
| End | TAA | 21.00 | 1.34 | 0.44 |
| End | TGA | 16.00 | 1.02 | 0.33 |

FIG. 1

SEQUENCE COMPARISON - SYNTHETIC TO NATIVE

```
      MetAspAsnAsnProAsnIleAsnGluCysIleProTyrAsnCysLeuSerAsnProG
480 CCATGGACAACAACCCAAACATCAACGAGTGCATCCCATACAACTGCCTCAGCAACCCAG 539
    |||||||  |||||  ||  ||||||||  ||  ||||||  ||  ||  ||    ||  ||||||  |
    CCATGGATAACAATCCGAACATCAATGAATGCATTCCTTATAATTGTTTAAGTAACCCTG

      luValGluValLeuGlyGlyGluArgIleGluThrGlyTyrThrProIleAspIleSerL
540 AGGTGGAGGTGCTCGGCGGCGAGAGGATCGAGACCGGCTACACCCCAATCGACATCAGCC 599
    |  ||  ||  ||   |  ||  ||  ||  ||  ||  ||  ||  |||||||||||||  ||    |
    AAGTAGAAGTATTAGGTGGAGAAAGAATAGAAACTGGTTACACCCCAATCGATATTTCCT

      euSerLeuThrGlnPheLeuLeuSerGluPheValProGlyAlaGlyPheValLeuGlyL
600 TCAGCCTCACCCAGTTCCTCCTCAGCGAGTTCGTGCCAGGCGCCGGCTTCGTTCTCGGCC 659
    |      ||  ||  ||  ||  ||    |  ||  ||  ||  ||  ||  ||  ||  ||  ||    |  ||  |
    TGTCGCTAACGCAATTTCTTTTGAGTGAATTTGTTCCCGGTGCTGGATTTGTGTTAGGAC

      euValAspIleIleTrpGlyIlePheGlyProSerGlnTrpAspAlaPheProValGlnI
660 TCGTGGACATCATCTGGGGCATCTTCGGCCCAAGCCAGTGGGACGCCTTCCCAGTGCAGA 719
    |  ||  ||  ||  ||  |||||  ||  ||  ||  ||     ||  |||||||  ||  ||  ||  ||  |
    TAGTTGATATAATATGGGGAATTTTTGGTCCCTCTCAATGGGACGCATTTCCTGTACAAA

      leGluGlnLeuIleAsnGlnArgIleGluGluPheAlaArgAsnGlnAlaIleSerArgL
720 TCGAGCAGCTCATCAACCAGAGGATCGAGGAGTTCGCCAGGAACCAGGCCATCTCTAGAC 779
    |  ||  |||  |  ||  ||||||  ||  ||  ||  ||  |||||  |||||||||  |||||  ||||||
    TTGAACAGTTAATTAACCAAAGAATAGAAGAATTCGCTAGGAACCAAGCCATTTCTAGAT

      euGluGlyLeuSerAsnLeuTyrGlnIleTyrAlaGluSerPheArgGluTrpGluAlaA
780 TTGAGGGCCTCAGCAACCTCTACCAGATCTACGCCGAGAGCTTCAGGGAGTGGGAGGCCG 839
    |  ||  ||  ||  ||||||  ||  ||  ||  ||  ||||||  ||     ||  ||  ||||||||||  ||  |
    TAGAAGGACTAAGCAATCTTTATCAAATTTACGCAGAATCTTTTAGAGAGTGGGAAGCAG

      spProThrAsnProAlaLeuArgGluGluMetArgIleGlnPheAsnAspMetAsnSerA
840 ACCCAACCAACCCAGCCCTCAGGGAGGAGATGCGCATCCAGTTCAACGACATGAACAGTG 899
    |  |||  ||  ||  ||||||   |  ||  ||  |||||||||  ||  ||  |||||  |||||||||||||
    ATCCTACTAATCCAGCATTAAGAGAAGAGATGCGTATTCAATTCAATGACATGAACAGTG

      la
900 CCCT 903
    ||||
    CCCT
```

FIG. 2

REACTION WITH KB72 AND KB73 TO DERIVE AMVBT2 FROM AMVBTS

```
KB72
5' ACAACCATGGACAACAACCCAAACATCAACGAGTGCATCCCATACAACTGCCTCAGCAACCCAGAGGTGGAGGTGC/
   3' - - - - - - - - - - - - - - - - - - - - - - - - - /
KB73

KB72(continued)
       /TCGGCGGCGAGAGGATCGAGACCGGCTAC - - - - - - - - - - - - - - - - - - - - - - - - - - 3'
       /- - - CTCTCCTAGCTCTGGCCGATGTGGGGTTAGCTGTAGTCGGAGTCGGAGTGGGTCAAGGAGGAGTCGCTCAAGCACGGTCCGCGGCCGAAGCACGAGCCTGATCAGGC 5'
KB73(continued)

       1. ANNEAL OLIGONUCLEOTIDES KB72 and KB73
       2. EXTEND WITH KLENOW POLYMERASE PLUS 4 DEOXYNUCLEOTIDE TRIPHOSPHATES

5' ACAACCATGGACAACAACCCAAACATCAACGAGTGCATCCCATACAACTGCCTCAGCAACCCAGAGGTGGAGGTGC/
3' TGTTGGTACCTGTTGTTGGGTTTGTAGTTGCTCACGTAGGGTATGTTGACGGAGTCGTTGGGTCTCCACCTCCACG/
       Nco I

5'(con't)  /TCGGCGGCGAGAGGATCGAGACCGGCTACACCCCAATCGACATCAGCCTCAGCCTCACCCAGTTCCTCCTCAGCGAGTTCGTGCCAGGCGCCGGCTTCGTGCTCGGACTAGTCCG 3'
3'(con't)  /AGCCGCCGCTCTCCTAGCTCTGGCCGATGTGGGGTTAGCTGTAGTCGGAGTCGGAGTGGGTCAAGGAGGAGTCGCTCAAGCACGGTCCGCGGCCGAAGCACGAGCCTGATCAGGC 5'
                                                                                                                  Spe I

       3. PHENOL EXTRACT TO INACTIVATE KLENOW
       4. DIGEST WITH Nco I AND Spe I TO REVEAL STICKY ENDS

5'    CATGGACAACAACCCAAACATCAACGAGTGCATCCCATACAACTGCCTCAGCAACCCAGAGGTGGAGGTGC/
3'        CTGTTGTTGGGTTTGTAGTTGCTCACGTAGGGTATGTTGACGGAGTCGTTGGGTCTCCACCTCCACG/
       Nco I

5'(con't)  /TCGGCGGCGAGAGGATCGAGACCGGCTACACCCCAATCGACATCAGCCTCAGCCTCACCCAGTTCCTCCTCAGCGAGTTCGTGCCAGGCGCCGGCTTCGTGCTCGGA 3'
3'(con't)  /AGCCGCCGCTCTCCTAGCTCTGGCCGATGTGGGGTTAGCTGTAGTCGGAGTCGGAGTGGGTCAAGGAGGAGTCGCTCAAGCACGGTCCGCGGCCGAAGCACGAGCCTGATC 5'
                                                                                                                  Spe I
```

FIG.3

REACTION WITH KB74 AND KB75 TO DERIVE AMVBT3 FROM AMVBT2

KB74
5' CAAGGCGCCGGCTTCGTTCTCGGCCTCGTGGACATCATCTGGGGCATCTTCGGCCCAAGCCAG/
3' - - - - - - - - - - - - - - - - - - - - - - - - - /
KB75

KB74(continued)
/TGGGACGCCTTCCCAGTGCAGA - - - - - - - - - - - - - - - - - - - - - - 3'
/ - TGCGGAAGGGTCACGTCTAGCTCGTCGAGTAGTTGGTCTCCTAGCTCCTCAAGCGGTCCTTGGTCCGGTAGAGATCTCC 5'
KB75(continued)

1. ANNEAL OLIGONUCLEOTIDES KB74 and KB75
2. EXTEND WITH KLENOW POLYMERASE AND 4 DEOXYNUCLEOTIDES TRIPHOSPHATES 5' CAAGGCGCCGGCTTCGTTCTCGGCCTCGTGGACATCATCTGGGGCATCTTCGGCCCAAGCCAG/
3' GTTCCGCGGCCGAAGCAAGAGCCGGAGCACCTGTAGTAGACCCCGTAGAAGCCGGGTTCGGTC/
Ban I 5'(con't) /TGGGACGCCTTCCCAGTGCAGATCGAGCAGCTCATCAACCAGAGGATCGAGGAGTTCGCCAGGAACCAGGCCATCTCTAGAGG 3'
3'(con't) /ACCCTGCGGAAGGGTCACGTCTAGCTCGTCGAGTAGTTGGTCTCCTAGCTCCTCAAGCGGTCCTTGGTCCGGTAGAGATCTCC 5'
Xba I 3. PHENOL EXTRACT TO INACTIVATE KLENOW
4. DIGEST WITH Ban I AND Xba I 5' GCGCCGGCTTCGTTCTCGGCCTCGTGGACATCATCTGGGGCATCTTCGGCCCAAGCCAG/
3' GCCGAAGCAAGAGCCGGAGCACCTGTAGTAGACCCCGTAGAAGCCGGGTTCGGTC/
Ban I 5'(con't) /TGGGACGCCTTCCCAGTGCAGATCGAGCAGCTCATCAACCAGAGGATCGAGGAGTTCGCCAGGAACCAGGCCATCT 3'
3'(con't) /ACCCTGCGGAAGGGTCACGTCTAGCTCGTCGAGTAGTTGGTCTCCTAGCTCCTCAAGCGGTCCTTGGTCCGGTAGAGATC 5'
Xba I

FIG. 4

REACTION WITH KB76 AND KB77 TO DERIVE AMVBT4 FROM AMVBT3

```
KB76
5' CGTCTAGACTTGAGGGCCTCAGCAACCTCTACCAGATCTACGCCGAGAGCTT/
3'  - - - - - - - - - - - - - - - - - - - - /
KB77

KB76(continued)
        /CAGGGAGTGGGAGGCCGACCCAAC - - - - - - - - - - - - - - - - - - - - 3'
        / -  CTCACCCTCCGGCTGGGTTGCTCACCCTCCGGCTGGGTTGGTTGGGTAGTCCCTCCTCTACGCGTAGGTCAAGTTGCTGTACTTGTCACGGGTC 5'
KB77(continued)
```

1. ANNEAL OLIGONUCLEOTIDES KB76 and KB77
2. EXTEND WITH KLENOW POLYMERASE AND 4 DEOXYNUCLEOTIDES TRIPHOSPHATES

```
5' CGTCTAGACTTGAGGGCCTCAGCAACCTCTACCAGATCTACGCCGAGAGCTT/
3' GCAGATCTGAACTCCCGGAGTCGTTGGAGATGGTCTAGATGCGGCTCTCGAA/
      Xba I
5'(con't)   /CAGGGAGTGGGAGGCCGACCCAACGAGTGGGAGGCCGACCCAACCAACCCAGCCCTCAGGGAGGAGATGCGCATCCAGTTCAACGACATGAACAGTGCCCAG 3'
3'(con't)   /GTCCCTCACCCTCCGGCTGGGTTGCTCACCCTCCGGCTGGGTTGGTTGGGTCGGGAGTCCCTCCTCTACGCGTAGGTCAAGTTGCTGTACTTGTCACGGGTC 5'
                                                                                                   Bsp 1286
```

3. PHENOL EXTRACT TO INACTIVATE KLENOW
4. DIGEST WITH Xba I AND Bsp 1286

```
5'     CTAGACTTGAGGGCCTCAGCAACCTCTACCAGATCTACGCCGAGAGCTT/
3'        TGAACTCCCGGAGTCGTTGGAGATGGTCTAGATGCGGCTCTCGAA/
      Xba I

5'(con't)   /CAGGGAGTGGGAGGCCGACCCAACGAGTGGGAGGCCGACCCAACCAACCCAGCCCTCAGGGAGGAGATGCGCATCCAGTTCAACGACATGAACAGTGCC 3'
3'(con't)   /GTCCCTCACCCTCCGGCTGGGTTGCTCACCCTCCGGCTGGGTTGGTTGGGTCGGGAGTCCCTCCTCTACGCGTAGGTCAAGTTGCTGTACTTGTC 5'
                                                                                              Bsp 1286
```

FIG. 5

EXPRESSION OF THE TOXIC PORTION OF CRY1A IN PLANTS

CROSS-REFERENCE TO RELATED APPLICATIONS

This application is a continuation of U.S. application Ser. No. 07/827,906, filed Jan. 30, 1992, which is a continuation of U.S. application Ser. No. 07/390,561, filed Aug. 7, 1989 now abandoned.

FIELD OF THE INVENTION

The present invention relates to the general field of genetic engineering and is directed, in particular, to improvements in the coding sequence for foreign genes to be expressed in the cells of higher plants.

BACKGROUND OF THE INVENTION

It is now possible reliably and repetitively to insert foreign genes into the germ line cells of higher plants, at least for certain species. A variety of techniques exist, notably *Agrobacterium*-mediated plant transformation and particle-mediated plant transformation, by which foreign genes can be introduced into the germ line plants in such a fashion that progeny of the plants will bear the gene of interest which is inserted. Accordingly, one area of research directed toward the creation of improved transgenic plants of potential commercial interest is in the insertion into plants of useful genes obtained from other species or classes of organisms so that the benefits of the gene product can be imbued into certain lines of higher plants. Examples of gene products in which effort has been directed toward their expression in plants cells include various toxins for control of insects, genes coding for various kinds of viral or other pathogen disease resistance, and genes coding for resistances to specific herbicides or antibiotics. In many of these cases the gene which is desired to be expressed in the plant cell comes from a procaryotic or viral organism. Some foreign genes may be from other species of plant or from other plants of the same species. When heterologous genes from these sources are inserted into plants, using promoters and expression cassettes which have been found operable and effective to express genes in plant cells, the results have been found to be sometimes uneven. There are apparent differences in either the transcription or translation levels of given coding sequences in plant tissues, even if the coding sequences are under the control of identical transcriptional promoters and terminators.

An example of this phenomenon has been found to occur with the gene for the delta-endotoxin crystal protein gene from the soil dwelling microorganism *Bacillus thuringiensis* (hereinafter referred to as the *B.t.* gene). A number of *B.t.* genes coding for homologous proteins have been cloned and sequenced by a variety of investigators throughout the world. Several of genetic constructs including one of the *B.t.* genes have been used to create chimeric plant expression gene constructions which are then transferred into the cells of plants. The various *B.t.* genes have been found to have significant differences in the DNA coding regions of the genes, although there is relatively high homology in the proteins for which they code. Nevertheless, the *B.t.* genes have characteristically been found to express relatively poorly in plant cells as compared to most other gene products which have been introduced into the cells of higher plants. The phenomenon of poor or low expression appears to have been experienced in all examples to date resulting from the introduction of native coding sequences for *B.t.* genes into plants, even though the expression cassettes and promoters and transcription terminators varied from experiment to experiment. One possible explanation for the observed phenomenon might be some feature of the native bacterial coding sequence itself.

As is known to all of ordinary skill in molecular biology, the genetic code of three nucleotide units, or codons, specifying particular amino acids, is degenerate. While a single amino acid is specified by each three nucleotide codon which makes up the genetic code found in DNA or RNA, because there are less amino acids possible than there are codon arrangements possible, most amino acids are specified by more than one codon sequence. For example, the amino acids serine, arginine, and leucine are all specified by any of six possible codons. It is thus possible to have nucleotide coding sequences for proteins which can differ significantly in their nucleotide sequence while specifying an identical amino acid sequence for the resultant protein.

SUMMARY OF THE INVENTION

The present invention is summarized as a method for constructing chimeric coding sequences for expression in plant cells in which the native coding sequence for a foreign gene to be expressed in plant cells is modified by substituting for the codons in the foreign coding region codons which are preferentially expressed in plants. The codons preferred for expression in plants are determined by analysis of the codon usage pattern of plant genes which are natively efficiently expressed in native plant tissues.

The present invention is further summarized in that a plant is engineered with a chimeric gene construct including a protein coding region constructed, and least in part, by oligonucleotide synthesis wherein the oligonucleotides are selected on the basis of preferred codon usage as determined by the usage of codons in genes which express well natively in plants.

It is an object of the present invention to enable the efficient construction of plant genes so as to obtain high steady-state levels of transcription and expression.

It is another object of the present invention to provide a *B.t.* gene construction which provides for high steady-state level of transcription and expression of the *B.t.* delta endotoxin protein in plant cells.

Other objects, advantages, and features of the present invention will become apparent from the following specification when taken in conjunction with the accompanying drawings.

BRIEF DESCRIPTION OF THE DRAWINGS

FIG. 1 is a table of preferred codon usage for use within the practice of the present invention as described further below.

FIG. 2 is a comparison of the coding regions of pAMVBTS (uppermost nucleotide sequence, nucleotides 1-424 of SEQ ID NO:1) and pAMVBT4 (lower nucleotide sequence, nucleotides 1–424 of SEQ ID NO:3).

FIG. 3 illustrates the sequence and assembly of oligonucleotides KB72 and KB73. The nucleotide sequence alignment illustrated above steps "1" and "2" shows the overlap between oligonucleotides KB72 (SEQ ID NO:4) and oligonucleotide KB73 (SEQ ID NO:5), before polymerase extension, in which nucleotides 85–105 of SEQ ID NO:4 are aligned with nucleotides of 87–107 of SEQ ID NO:5. The nucleotide sequence alignment illustrated between steps "2" and "3" represents the aligned sequences SEQ ID NO:4 and SEQ ID NO:5 after polymerase extension, the upper sequence corresponding to SEQ ID NO:6, and the lower sequence, the reverse complement of SEQ ID NO:6, corresponding to SEQ ID NO:7. The nucleotide sequence alignment below step "4" represents the extended sequence illustrated between steps "2" and "3" after digestion with the restriction endonucleases NcoI and SpeI, the upper sequence in the alignment corresponding to SEQ ID NO:8, and the lower sequence in the alignment corresponding to SEQ ID NO:9.

FIG. 4 illustrates the sequence and assembly of oligonucleotides KB74 and KB75. The nucleotide sequence alignment illustrated above steps "1" and "2" in FIG. 4 shows the overlap between oligonucleotides KB74 (SEQ ID NO:10) and oligonucleotide KB75 (SEQ ID NO:11), before polymerase extension, in which nucleotides 68–85 of SEQ ID NO:10 are aligned with nucleotides 62–79 of SEQ ID NO:11. The nucleotide sequence alignment illustrated between steps "2" and "3" represents the aligned sequences SEQ ID NO:10 and SEQ ID NO:11 after polymerase extension, the upper sequence corresponding to SEQ ID NO:13, and the lower sequence, the reverse complement of SEQ ID NO:13, corresponding to SEQ ID NO:14. The nucleotide sequence alignment below step "4" represents the extended sequence illustrated between steps "2" and "3" after digestion with the restriction endonucleases BanI and XhaI, the upper sequence in the alignment corresponding to SEQ ID NO:14, and the lower sequence in the alignment corresponding to SEQ ID NO:15.

FIG. 5 illustrates the sequence and assembly of oligonucleotides KB76 and KB77. The nucleotide sequence alignment illustrated above steps "1" and "2" in FIG. 5 shows the overlap between oligonucleotides KB76 (SEQ ID NO:16) and oligonucleotide KB77 (SEQ ID NO:17), before polymerase extension, in which nucleotides 63–76 of SEQ ID NO:16 are aligned with nucleotides 75–94 of SEQ ID NO:17. The nucleotide sequence alignment illustrated between steps "2" and "3" represents the aligned sequences SEQ ID NO:16 and SEQ ID NO:17 after polymerase extension, the upper sequence corresponding to SEQ ID NO:18, and the lower sequence, the reverse complement of SEQ ID NO:18, corresponding to SEQ ID NO:19. The nucleotide sequence alignment below step "4" represents the extended sequence illustrated between steps "2" and "3" after digestion with the restriction endonucleases XbaI and BspI, the upper sequence in the alignment corresponding to SEQ ID NO:20, and the lower sequence in the alignment corresponding to SEQ ID NO:21.

DETAILED DESCRIPTION OF THE PRESENT INVENTION

Figure 6:
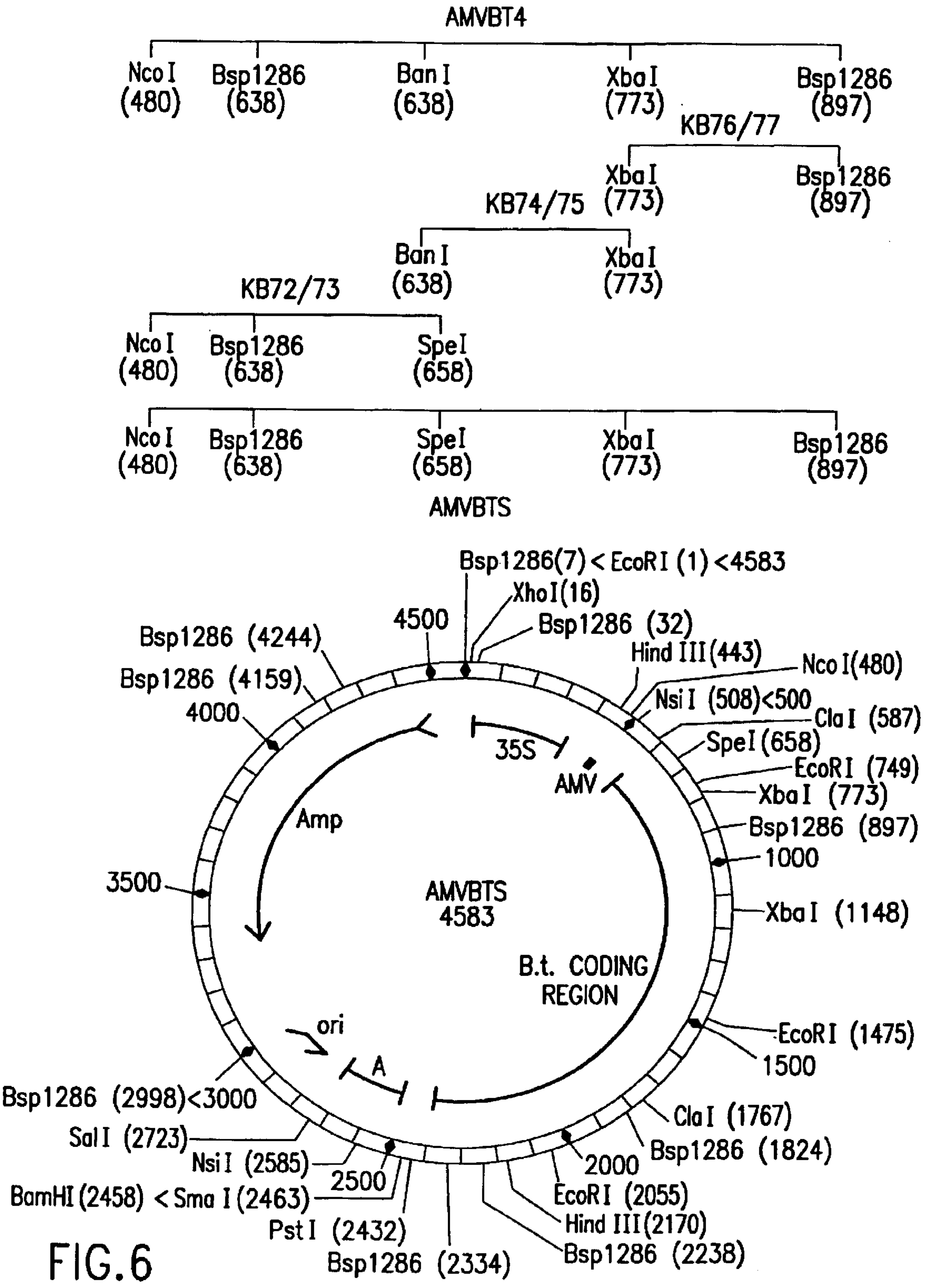
FIG. 6 illustrates the assembly of the oligonucleotides and their insertion into pAMVBTS.

The principle of the present invention is based on an insight derived from scientific investigation into the problem of expressing significant levels of the *B.t.* gene in plant cells. As already mentioned above, previous reports of the creation of chimeric expression constructions including the *B.t.* gene and the introduction of those constructions into the genome of plants have given rise to relatively low levels of expression and low levels of measurable mRNA. It can be demonstrated that a *B.t.* expression construction using a plant promoter known to work well with other genes, such as the cauliflower mosaic virus 35S (CaMV 35S) generates a lower steady-state level of mRNA in plant cells than other genes inserted behind the same promoter. Since the problem appeared to be organic to the native *B.t.* coding sequence itself, the nature of that coding sequence itself was investigated in detail. Such analysis revealed one feature in particular that seemed to be a relatively unique feature of all reported *B.t.* genes. All of the reported native *B.t.* genes seem to have a high proportion of A and T nucleotide basis in their coding sequence, relative to other bacterial coding sequences that had been found to be more easily expressed in plants. The reason for this is obscure. Nevertheless, it seems that different coding sequences coding for identical proteins could have differing characteristics of mRNA stability or of interaction with the translational machinery of a given type of cell. For example, the chemical binding energy and secondary structure of mRNAs can be different depending on the relative proportions of the nucleotide pairs. It is also quite possible that the nucleotide content of a given mRNA may affect the strength of the interaction of that mRNA with ribosome.

Regardless of which of these, or if other, theories are appropriately correct to explain the difference in nucleotide content of the *B.t.* gene from other genes which express well in plant cells, one could logically assume that the plant transcriptional and translational systems which had evolved over time within the cells of plants themselves would have evolved to have some optimal or increased efficiency for those genes important to the plant system itself. Thus it becomes unnecessary to understand the exact system by which an mRNA of a certain nucleotide content might be preferred over an mRNA with a different nucleotide content, if the phenomenon can be used to advantage simply by examining the coding regions known to express well in plants to determine the nucleotide and codon usage characteristics of those molecules.

To determine those codons which are therefore "preferred" for usage in plant cells, or those which are preferentially expressed in plant cells, it was determined that a logical place for inquiry would be plant genes themselves, to the extent they are known. Certain public sequence data base services (for example GenBank) contained within them many sequences for plant genes which have been sequenced and had their sequence published. It is therefore possible to examine those published sequences to determine within those plant genes which codons are preferred compared to others which are not preferred. In order to accomplish this objective, the GenBank and EMBL public sequence data bases were utilized. In order to correct for possible bias due to the over representation of certain kinds of genes, within the limited number of plant gene sequences which are contained in present data bases, a number of limiting assumptions were made in the compilation. A tailored list of genes was created intended to avoid placing over emphasis on the families of genes which have been most studied. Therefore, for example, only a limited number of storage protein genes were included within the information base on codon usage. A representative storage protein gene was selected from each of maize, soybean and other important crops, and the remaining storage protein genes were considered not to be distinct from these representative sequences. Other gene types which were also over represented in the publicly available data bases, such an heat shock genes, were similarly selected from. The information was further edited to include only complete coding sequence information where available. Information was pooled into one common information base, regardless of plant species from which the gene sequence was derived. Data was not species specific only because there are not sufficient numbers of reported gene sequences from any one given plant species of interest to be sufficiently statistically useful in and of itself. Data from gene that express in different tissues or different periods of development, but are similar, were also pooled on the theory that there are not enough examples in the kinds of genes available to provide a significant consensus sequence.

As research in the molecular biology of plant genes continues, the knowledge base of published plant gene sequences may expand to the point where more specificity in determining preference of codon usage may be possible. For example, it may develop that certain plant species may have a preference for a given pattern of codon usage over that pattern preferred by another species. There may also be differences in codon usage among cell or tissue types in the same species. Thus, while the tabulation of plant codon usage developed here is generally useful and probably a good approximation of an optimum pattern of usage for plants in general, it may be preferred to a given tissue or plant to have a modified table of codon usage more specific to that tissue or plant.

Once the information base of publicly available plant gene sequences was assembled, a codon usage table for plant genes in general was compiled by an appropriate computer program, which analyzed all of the codons used in all of the plant gene sequences contained in the information base. The table representing the results of this compilation is contained in FIG. 1 herein. This table shows the frequency of use of the various plant codons contained within the information base generated from the publicly available plant gene sequences. The farthest right number associated with each codon is the percentage that that codon is utilized by the plant gene sequences in the public sequence data base as a proportion of all of the codons which code for the same amino acid. Thus, for amino acids for which there is only one codon, such as methionine and tryptophan, the codon has a usage factor of 1.0 indicating that it is used all the time when that amino acid is specified. As another example, for the amino acid aspartate, the codon GAT is used 45% of the time that the amino acid is specified in the total of all the plant genes in the information base, while the alternative codon for aspartate, GAC, is used at a frequency of 55% of the time of the coding sequences in the data base.

An examination of the usage table contained in FIG. 1 reveals strong biases in codon usage among the plant genes for several amino acids that have degenerate codons for the same amino acid. As an example, for the amino acid lysine, in plant genes 81% of the time where the amino acid is to be specified, the codon AAG is utilized while only 19% of the time that the amino acid is to be specified is the codon AAA utilized. As another example, of the six possible codons which code for the amino acid leucine, four of the codons represent 92% of the total leucine codon usages, while the two codons TTA and CTA are used a total of only 8% of the occurrences of a leucine codon within the coding sequences of all of the plant genes in the information base. Similar biases, which vary in strength, are present for almost all of the amino acids.

It was then possible to compare the codon usage for the native *B.t.* coding sequence with the codon usage frequency of native plant genes. The results were quite striking, in that in most instances where the table of preferred codon usage for plant genes shows a bias toward a particular codon usage, the native coding region for the *B.t.* gene showed precisely the opposite preference of use. As an example, for leucine, a preferred codon found in the native coding region of the *B.t.* gene was the codon TTA, which appeared 45% of the time that the amino acid leucine was to be specified by the *B.t.* gene, while that codon is the least preferred of all of the possible leucine codons in plant genes, representing only 3% of the total codon usage. In the native *B.t.* coding sequence it was determined that the twenty-six TTA leucine codons represented 4% of the total of the amino acids in the protein which indicated that the native coding region for the *B.t.* gene is not typical of what is found in a native plant gene. An examination of other chimeric constructions including other bacterial genes which have been found to express well in plants, no similar problems could be uncovered. Most gene products which have been found to express well in plants conformed well to the plant codon usage table, with there seeming to be some correlation between the level of expression and the highest correlation to the codon usage preferred by plants as represented by the codon usage table of FIG. 1.

Using this data it was then possible to construct a synthetic *B.t.* coding region for a chimeric gene composed principally of codons selected from those codons which are preferentially expressed by plants as determined by the usage pattern of plants illustrated in FIG. 1. Rather than synthesizing the entire coding region of the *B.t.* gene, it was first decided to synthesize the 5' end of the coding sequence, and to determine the effect of the codon substitution in that region on the overall expression of the gene product by the plant cells. Therefore, using the table of preferred codon usage as a guide, a nucleotide sequence was designed for the first 138 codons of the *B.t.* coding region. The codons for each codon set of this synthesized *B.t.* region were selected to code for the identical amino acids present in the native procaryotic protein, but were selected to be the particular codon that had the highest frequency of use according to the plant gene codon analysis described above. In other words, the chimeric nucleotide coding sequence was specifically constructed to code for the expression of the same amino acid but was made up of codons different from that in the native organism and selected from those codons determined to be preferentially efficiently expressed by native plant genes. These changes were made on a pre-existing *B.t.* expression plasmid, referred to as pAMVBTS, previously used by the inventors here to express the *B.t.* gene in plants. FIG. 2 attached hereto shows a sequence comparison of the original coding region for nucleotides 480 through 903 of the pAMVBTS gene aligned with the synthetic coding region specified as described above. Nucleotide homologies between the two sequences are noted. The sequence in pAMVBTS is the sequence natively present in the HD-1-DIPEL subspecies *Kurstaki* gene of *Bacillus thuringiensis.* It is a feature of this alignment table that it can be seen that many of the nucleotides in the third position of the codon have been altered. This is to be expected since the third position is the most degenerate position to conserve amino acid code. The most frequent change of actual individual nucleotide is from an A in the third position in the native procaryotic sequence to another nucleotide, usually C or G, in the chimeric synthetic sequence. The overall effect of the changes was an increase in C and G content and a decrease in A and T content.

Since the synthesis of an oligonucleotide exceeding 400 base pairs in length is rather difficult, the actual synthesis of the synthetic coding region, described below, was constructed by constructing six separate oligonucleotides which were composed of three separate overlapping pairs. The overlapping pairs were hybridized and then extended into complete duplexes by Klenow polymerase. The three sets of oligonucleotides were arranged so that they would be easily annealed end-to-end to create the entire synthetic coding region. The sequence of the particular oligonucleotides is given in the attached drawings so that construction of these same oligonucleotides can be accomplished by those skilled in the art.

The synthetic coding region thus constructed serves as a protein coding region which can be combined with flanking regulatory sequences for creating a chimeric gene for transformation into a plant to create transgenic plants expressing the *B.t.* protein. Any otherwise suitable regulatory sequences, such as promoters, 5' non-coding sequences and polyadenylation sequences, are effective with this coding region. The chimeric gene may be inserted through any conventional transformation technique into any plants capable of transformation. While the results indicated below have been conducted with the model species tobacco, the use of tobacco is principally as the result of the ease of transformation and regeneration of tobacco plants, thus making it relatively easy to achieve transgenic expression. Results with the native *B.t.* coding region have indicated that expression cassettes active to express the *B.t.* coding region in tobacco are similarly active in cotton and in other plants. Since the preferred codon usage table of FIG. 1 was derived by reference to all plants, rather than just tobacco, there is good reason to believe and expect that the increased efficiency of expression achieved in tobacco through the use of the method and coding region of the present invention will be equally applicable in other plant species, as it is in tobacco, as demonstrated by the results here.

It also becomes obvious to one skilled in the art that the method is used with the particular procaryotic gene described and illustrated in the present invention is equally applicable to other procaryotic or even eukaryotic, genes which happen not to express well in plants. The results of this procedure demonstrate that at least one factor in the relatively low expression level of the procaryotic *B.t.* protein in plants is due to the actual makeup of the codon usage pattern of the particular procaryotic gene. Other procaryotic or eukaryotic genes which similarly use a large number of codons which are not among those preferentially expressed by plants may also be altered in the similar fashion. Again the actual protein made by the plant can be identical in the amino acid sequence to the protein encoded by the native foreign gene. Only the codons are switched, not the amino acid that is coded. Therefore it is possible to express many foreign proteins effectively and efficiently in plant cells and still to produce a protein identical in amino acid sequence to the native protein while still gaining the efficiencies possible using the transcriptional and translational machinery of plants more effectively.

This method may even be applicable to some plant genes. It can be readily imagined why some plant genes may be advantageously expressed at less than total efficiency, and one mechanism which might be used is inefficiencies in the pattern of codon usage. As an optimal pattern of usage is developed, it may be possible to enhance the level of a native plant gene by similarly changing the pattern of its codon usage and returning the modified gene to a plant of the same or different species.

As an examination of the following Examples will reveal to one skilled in the art, the substitution of plant preferred codons in a plant expression cassette results in an increased level of efficiency in expression of the engineered protein. In the following example, the coding region of the protein expression cassette was altered by as few as 59 to as many as 138 codons, all at the amino terminal end of the protein or the 5' end of the coding region. Since the results did not seem to vary greatly based on the length of the substituted codons, it is possible that the increased expressional efficiency is due principally to the substitutions at the amino-terminal, or 5', end of the coding sequence, perhaps those in the first 25 codons. One possible explanation for this might be increased efficiency in binding to ribosomes. If true, this would suggest that entire coding regions need not be altered to gain a relatively significant increase in efficiency of expression, merely the amino-terminal end of the coding region, for perhaps about 25 codons. Performing such a codon substitution for the remaining portion of the coding region might still be expected to increase efficiency of expression, although perhaps less dramatically.

The present invention will be understood to be more generalized from a consideration of the following example of the practice of this invention.

EXAMPLES

As described above, a chimeric synthetic coding sequence for the first 138 codons of the *B.t.* gene coding sequence was constructed. This coding sequence was constructed by synthesizing six oligonucleotides which were grouped in three overlapping pairs. Each single stranded oligonucleotide was then hybridized to its partner which it overlapped. The two joined oligonucleotides, now partially double-stranded, were extended into complete duplexes through the use of Klenow polymerase. The oligonucleotide pairs were designed to have overlapping 3' ends in each pair to form priming sites for the action of the polymerase. The ends of each pair were designed to include restriction sites for efficient joining of the ends of the double-stranded oligonucleotides together into the *B.t.* expression plasmid.

The process began with the construction of the six oligonucleotides. The complete sequences for all six oligonucleotides and their assembly into the three double-stranded coding region segments is illustrated effectively in FIGS. 3, 4 and 5. The particular oligonucleotides were designated KB72-KB77. As illustrated, for example, in FIG. 3, the oligonucleotide KB72 was constructed so as to have a complementary 21 nucleotides to the end of the oligonucleotide KB73. The two oligonucleotides were then annealed and extended with a Klenow polymerase plus four deoxynucleotide triphosphates. The annealed double-stranded DNA was then processed through a phenol extract to inactivate the Klenow polymerase and was digested with Nco I and Spa I to reveal the sticky ends illustrated in FIG. 3. Similarly as can be seen with reference to FIGS. 4 and 5, the oligonucleotides KB74 and KB75 were annealed, extended, and digested to result in a fragment having sticky ends resulting from digestion by the Ban I and Xba I and the oligonucleotides KB76 and KB77 were hybridized, annealed and digested to result in a fragment having sticky ends digested by Xba I and Bsp 1286.

The assembly of the three coding sequence fragments into the genome of pAMVBTS was constructed in three stages resulting in the sequential construction of three plasmids, pAMVBT2, pAMVBT3 and pAMVBT4, each one of which had a sequentially greater portion of its coding region substituted by the synthetic sequence. The process began with the plasmid pAMVBTS as illustrated in FIG. 6.

Before insertion into the actual expression plasmid, the three blunt ended duplex fragments were first cloned into pUC12 and the synthetic DNA was sequenced to confirm that the synthesis had been correct. The synthetic inserts were freed from pUC12 by preparative digestion of the plasmids with the appropriate restriction enzymes to generate the required sticky ends. The fragments were purified from agarose gels.

The plasmid pAMVBTS was digested with Nco I and Spe I and the vector was purified away from the small 178 nucleotide fragment which had been excised from the plasmid. The synthetic fragment containing both KB72 and KB73 was then ligated with the larger portion of the pAMVBTS vector and the *E. coli* strain MM294 was transformed to ampicillin resistance. The resulting plasmid pAMVBT2 was identified by minipreps. This plasmid, pAMVBT2 was thus a complete plant expression plasmid containing the 35S promoter from cauliflower mosaic virus, a 5' non-coding region from the alfalfa mosaic virus, a *B.t.* coding region coding for the approximately 72 kilodalton Amino-terminal toxin portion of the native *Bacillus thuringiensis* delta endotoxin protein, but which differed from the native sequence by the substitution of the original native 59 codons with codons preferred by plants, followed by a polyadenylation sequence derived from nopaline synthase.

The plasmid pAMVBT2 was then digested with Ban I and partially digested with Xba I and the vector was purified to remove 132 base pair fragment released by these enzymes. The synthetic fragment formed from the oligonucleotides KB74 and KB75 was ligated to this vector and transformed into *E. coli* strain MM294 which was transformed to ampicillin resistance. The plasmid pAMVBT3 was identified by miniplasmid screening. Annealing of this insert into the larger portion of pAMVBT2 destroyed the Spe I site used in the construction of pAMVBT2. The amino acid specified by the Spe I recognition site did not conform to the codon usage table as specified by the preferred codon usage table of FIG. 1, but was a convenient site to retain until the construction of pAMVBT3. The plasmid pAMVBT3 was similar in all respects to pAMVBT2 with the exception that the substitution of codon usage from the native sequence had been extended for another 45 codons as compared to pAMVBT2.

To construct pAMVBT4, pAMVBT3 was first digested with Xba I and Cla I. The resulting 3,589 base pair fragment including the amino and carboxyl-termini of the *B.t.* toxin coding sequence and the rest of the expression cassette was purified away from the two smaller fragments, of 619 and 375 base pairs, released by the double digestion with these enzymes. The plasmid pAMVBT3 was then digested in a second reaction with Bsp 1286 and Cla I and the small fragment corresponded to the internal region of the *B.t.* toxin coding sequence between nucleotides 897 and 1767 with Bsp 1286 and Cla I sticky ends was purified. A ligation reaction was then conducted between the 3589 base pair vector from pAMVBT3 plus the 870 base pair coding region of pAMVBT3 (from the Bsp1286 site to the Cla I site) and the synthetic duplex of KB76 and KB77. The resulting plasmid was transformed into *E. coli* strain MM294, which was selected for ampicillin resistance, and the desired plasmid pAMVBT4 was again identified by plasmid minipreps.

Each of the plasmids pAMVBT2, pAMVBT3 and pAMVBT4 were individually co-integrated into the carrier plasmid pTV4. The plasmid pTV4 is contained within a plasmid pTV4AMVBTSH, which is ATCC Accession Number 53636, and can be readily retrieved from this plasmid by digestion with Xho I to completion, phenol extraction and ethanol precipitation after which the resulting plasmids can be religated, transformed into *E. coli*, and selected for sulfadiazine resistance. The sulfadiazine resistant colonies will contain the plasmid pTV4.

The plasmid pTV4 is a carrier plasmid containing a unique Xho I site bounded in one direction by a synthetic consensus right border sequence similar to the right border of T-DNA from *Agrobacterium tumefaciens*, and in the other direction, a complete expression cassette for the kanamycin resistance trait as conditioned by the plant expression gene APH-II, and a synthetic consensus left border sequence similar to the left border of *Agrobacterium* T-DNA. The plasmids pAMVBT2, pAMVBT3 and pAMVBT4 can be digested at their unique Xho I site, which is $_5$' to the coding region for the *B.t.* expression cassette, and ligated into copies of pTV4, also digested with Xho I, to result in complete transformation cassette, including the *B.t.* coding gene for kanamycin resistance, and left and right T-DNA borders suitable for transformation into plants.

These co-integrations were constructed and the three resulting transformation plasmids were conjugated into *A tumefaciens* strain EHA101 in a manner similar to that described in Barton, et al., *Cell,* 32, pp. 1033–1043 (1983). Seeds of tobacco were surface sterilized and germinated on Murasige and Skoog (MS) medium. Aseptically grown immature stems and leaves were then inoculated with overnight cultures of *A. tumefaciens* harboring the appropriate transformation plasmid. Following 48 to 72 hours of incubation at room temperature on a regeneration medium (MS medium containing 1 micrograms per ml of kinetin), cefotaxime (at 100 micrograms per ml) and vancomycin (at 250 micrograms per ml) were applied to kill the *Agrobacteria*, and kanamycin (at 100 micrograms per ml) was applied to select for transformant plant tissues. After approximately six weeks, with media changes performed at two week intervals, shoots appeared. The shoots were excised and placed in rooting medium containing 25 micrograms per ml kanamycin until roots were formed, which occurred in 1 to 3 weeks. After roots were formed, the plants were transferred to a commercial soil potting mixture for growth into mature plants. Insect toxicity tests were conducted on leaves of the resulting whole, intact, although small, tobacco plants.

Insect eggs of tobacco hornworm (*Manduca sexta*) were hatched on mature, wild-type tobacco plants. Larvae of the insects were allowed to graze for 1 to 3 days on wild-type plants prior to transfer to test plants. Since mature tobacco plants contain higher levels of secondary metabolites than freshly regenerated plants, the feeding of the larvae on the older plants made the larvae less sensitive to toxins than neonatal larvae. This was done to reduce the sensitivity of the larvae and this distinction proved useful in distinguishing between variations in the toxin produced in the transgenic plants. Tobacco hornworms were placed directly on the leaves of the young wild-type plants and on recombinant plants in number of 2 to 4 larvae per plant per test with up to 6 successive tests conducted per plant. Tests were conducted and the plants were graded as to their toxicity to the larvae. The plants were considered to be "killers" if all of the larvae grazing on the leaves of the plants ultimately terminated. The plants were rated relative to each other on the length of time and degree of feeding necessary before the "killer" plants caused death of the hornworms. A rating of "9" was indicative of a strongly resistant plant, where the high level of toxin present caused rapid cessation of feeding and early death. A rating of "5" or less indicated moderate toxicity, in which generally one or more days of limited feeding occurred before larval death.

Shown in Table I is a summary of the results of the hornworm feeding trials conducted with these three plasmids as compared to the plasmid pTVAMVBTSH which contains the native coding sequence derived from the native bacteria. The results illustrate that the number of total killers per portion of the total number of plants tested was not significantly greater for the plants with the synthetic sequence as compared to the plants which had been engineered with the procaryotic sequence. However, of those plants which exhibited toxicity to the hornworms, the plants which had the synthetic sequences exhibited a much more uniform and greater toxicity to the hornworms. A logical explanation for the observed phenomenon is that the nature of the coding sequence did not significantly increase or decrease recombinations or defects in genetic insertion into the transgenic plants and thus the total number of expressing plants would not be expected to be much different for the synthetic sequence as opposed to the native sequence. It is also possible that a certain number of the insertions occur at site-specific locations which result in poor expression of the inserted DNA. However, for those inserts which did result in expression of the toxicity trait to the insects, all of the plants containing the synthetic sequence exhibited a desirable level of mortality figures for the feeding larvae. This would indicate that the proteins were expressed more efficiently once inserted properly into the transgenic plants. In other words, the rate of insertion of expressing *B.t.* genes into plants had not increased but the level of expression and resulting effectiveness of the insert once made showed significant improvement. Use of Northern blotting has confirmed that transformants of tobacco containing pAMVBT2, pAMVBT3 or pAMVBT4 DNAs generally contain much higher steady-state levels of *B.t.* toxin mRNA than do transformants containing pAMVBT5 constructs. Also, immunoblotting has shown that pAMVBT5 transformants that are "killers" in general have much lower levels of toxin protein than do "killers" with pAMVBT2, pAMVBT3 or pAMVBT4 constructs. These results further support the concept that the codon substitutions in pAMVBT2, pAMVBT3 and pAMVBT4 result in more efficient expression of these genes in plants.

TABLE I

| Plasmid | Total Tested | Total Killers | No. Rated 9 | No. Rated 8 | No. Rated 7 | No. Rated 6 |
|---|---|---|---|---|---|---|
| pTVAMVBTSH | 52 | 20 | 2 | 12 | 2 | 4 |
| pTVAMVBT2 | 12 | 10 | 5 | 5 | 0 | 0 |
| pTVAMVBT3 | 37 | 17 | 10 | 7 | 0 | 0 |
| pTVAMVBT4 | 61 | 15 | 6 | 9 | 0 | 0 |

It has been previously demonstrated that transgenic traits introduced into plants by the methods described here are fully inheritable by normal Mendellian inheritance and the traits introduced as described herein have been shown to be so inheritable.

In order to enable others of ordinary skill in the art to easily practice the present invention and other related inventions, certain deposits have been made, all hosted *E. coli*, with the American Type Culture Collection, 12301 Park Lawn Avenue, Rockville, Md. U.S.A. on the dates listed below and with the following ATCC accession numbers. Similar deposits have been made with the Cetus Master Culture Collection maintained by Cetus corporation, Emeryville, Calif., and the CMCC accession numbers for those cultures are also given below. All deposits made with the ATCC have been in accordance with the Budapest Treaty.

| Plasmids | CMCC No. | ATCC No. | ATCC Deposit Date |
|---|---|---|---|
| pAMVBTS | 3137 | 53637 | June 24, 1987 |
| pTV4AMVBTSH | 3136 | 53636 | June 24, 1987 |

The construction of the oligonucleotides described in this patent application can be made without the necessity for plasmid starting materials since the sequence of the oligonucleotides is given in FIGS. 2 through 5 above.

The present invention is not to be understood to be limited in scope by the microorganisms or plasmids deposited herein since the deposited embodiment is intended as a single illustration of one aspect of the invention and to enable a single illustrative practice of the invention, and any microorganisms, plasmids or other nucleotides which are functionally equivalent or within the scope of this invention. Indeed, various modifications of the invention in addition to those shown and described herein will become apparent to those skilled in the art from the foregoing description and fall within the appended claims.

We claim:

1. A synthetic gene nucleic acid encoding an approximately 72 kD amino terminal toxic portion of a Cry1A protein of the *Bacillus thuringiensis* kurstaki subspecies HD-1, wherein the nucleic acid comprises:

a) SEQ ID NO:1, which encodes the amino terminal 138 amino acids of said protein, fused in frame to b) a nucleic acid encoding the remainder of said toxic portion of the Cry1A protein, wherein each of the codons are selected from the codons set forth in FIG. 1 as being used at the highest frequency in plants.

2. A synthetic nucleic acid encoding an approximately, 72 kD amino terminal toxic portion of a Cry1A protein of the *Bacillus thuringiensis* kurstaki subspecies HD-1, wherein each of the codons in said nucleic acid is selected from the codons set forth in FIG. 1 as being used at the highest frequency in plants.

3. A nucleic acid encoding a toxic portion of a Cry1A protein encoded by *Bacillus thuringiensis* kurstaki subspecies HD-1, wherein each codon in said nucleic acid specifying a given amino acid is selected from the codons used at the highest frequency in plants as set forth in FIG. 1.

* * * * *

UNITED STATES PATENT AND TRADEMARK OFFICE

CERTIFICATE OF CORRECTION

PATENT NO. : 6,833,449 B1
DATED : December 21, 2004
INVENTOR(S) : Barton et al.

It is certified that error appears in the above-identified patent and that said Letters Patent is hereby corrected as shown below:

Column 21,
Line 63, "synthetic gene nucleic acid" should read -- synthetic nucleic acid --.

Signed and Sealed this

Sixth Day of December, 2005

JON W. DUDAS
*Director of the United States Patent and Trademark Office*

SEQUENCE LISTING

```
<160> NUMBER OF SEQ ID NOS: 21

<210> SEQ ID NO 1
<211> LENGTH: 424
<212> TYPE: DNA
<213> ORGANISM: Artificial Sequence
<220> FEATURE:
<221> NAME/KEY: CDS
<222> LOCATION: (3)..(422)
<223> OTHER INFORMATION: Protein sequence is expressed by protein coding
      region of either BT4 or BTS sequence

<400> SEQUENCE: 1

cc atg gac aac aac cca aac atc aac gag tgc atc cca tac aac tgc        47
   Met Asp Asn Asn Pro Asn Ile Asn Glu Cys Ile Pro Tyr Asn Cys
     1               5                  10                  15

ctc agc aac cca gag gtg gag gtg ctc ggc ggc gag agg atc gag acc       95
Leu Ser Asn Pro Glu Val Glu Val Leu Gly Gly Glu Arg Ile Glu Thr
                 20                  25                  30

ggc tac acc cca atc gac atc agc ctc agc ctc acc cag ttc ctc ctc      143
Gly Tyr Thr Pro Ile Asp Ile Ser Leu Ser Leu Thr Gln Phe Leu Leu
```

-continued

```
            35                  40                  45

agc gag ttc gtg cca ggc gcc ggc ttc gtt ctc ggc ctc gtg gac atc       191
Ser Glu Phe Val Pro Gly Ala Gly Phe Val Leu Gly Leu Val Asp Ile
        50                  55                  60

atc tgg ggc atc ttc ggc cca agc cag tgg gac gcc ttc cca gtg cag       239
Ile Trp Gly Ile Phe Gly Pro Ser Gln Trp Asp Ala Phe Pro Val Gln
    65                  70                  75

atc gag cag ctc atc aac cag agg atc gag gag ttc gcc agg aac cag       287
Ile Glu Gln Leu Ile Asn Gln Arg Ile Glu Glu Phe Ala Arg Asn Gln
 80                 85                  90                  95

gcc atc tct aga ctt gag ggc ctc agc aac ctc tac cag atc tac gcc       335
Ala Ile Ser Arg Leu Glu Gly Leu Ser Asn Leu Tyr Gln Ile Tyr Ala
               100                 105                 110

gag agc ttc agg gag tgg gag gcc gac cca acc aac cca gcc ctc agg       383
Glu Ser Phe Arg Glu Trp Glu Ala Asp Pro Thr Asn Pro Ala Leu Arg
           115                 120                 125

gag gag atg cgc atc cag ttc aac gac atg aac agt gcc ct                424
Glu Glu Met Arg Ile Gln Phe Asn Asp Met Asn Ser Ala
       130                 135                 140


<210> SEQ ID NO 2
<211> LENGTH: 140
<212> TYPE: PRT
<213> ORGANISM: Artificial Sequence
<220> FEATURE:
<223> OTHER INFORMATION: Protein sequence is expressed by protein coding
      region of either BT4 or BTS sequence

<400> SEQUENCE: 2

Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Pro Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala
    130                 135                 140


<210> SEQ ID NO 3
<211> LENGTH: 424
<212> TYPE: DNA
<213> ORGANISM: BTS (original sequence of HD-1-dipel subsp. kurstaki
      gene)

<400> SEQUENCE: 3

ccatggataa caatccgaac atcaatgaat gcattcctta taattgttta agtaaccctg      60

aagtagaagt attaggtgga gaaagaatag aaactggtta caccccaatc gatatttcct     120

tgtcgctaac gcaatttctt ttgagtgaat ttgttcccgg tgctggattt gtgttaggac     180
```

-continued

```
tagttgatat aatatgggga atttttggtc cctctcaatg ggacgcattt cctgtacaaa    240

ttgaacagtt aattaaccaa agattagaag aattcgctag gaaccaagcc atttctagat    300

tagaaggact aagcaatctt tatcaaattt acgcagaatc ttttagagag tgggaagcag    360

atcctactaa tccagcatta agagaagaga tgcgtattca attcaatgac atgaacagtg    420

ccct                                                                 424


<210> SEQ ID NO 4
<211> LENGTH: 105
<212> TYPE: DNA
<213> ORGANISM: Artificial Sequence
<220> FEATURE:
<223> OTHER INFORMATION: Description of Artificial Sequence: KB72
      oligonucleotide

<400> SEQUENCE: 4

acaaccatgg acaacaaccc aaacatcaac gagtgcatcc catacaactg cctcagcaac     60

ccagaggtgg aggtgctcgg cggcgagagg atcgagaccg gctac                    105


<210> SEQ ID NO 5
<211> LENGTH: 107
<212> TYPE: DNA
<213> ORGANISM: Artificial Sequence
<220> FEATURE:
<223> OTHER INFORMATION: Description of Artificial Sequence:  KB73
      oligonucleotide

<400> SEQUENCE: 5

cggactagtc cgagcacgaa gccggcgcct ggcacgaact cgctgaggag gaactgggtg     60

aggctgaggc tgatgtcgat tggggtgtag ccggtctcga tcctctc                  107


<210> SEQ ID NO 6
<211> LENGTH: 191
<212> TYPE: DNA
<213> ORGANISM: Artificial Sequence
<220> FEATURE:
<223> OTHER INFORMATION: Description of Artificial Sequence: KB72
      oligonucleotide annealed and extended

<400> SEQUENCE: 6

acaaccatgg acaacaaccc aaacatcaac gagtgcatcc catacaactg cctcagcaac     60

ccagaggtgg aggtgctcgg cggcgagagg atcgagaccg gctacacccc aatcgacatc    120

agcctcagcc tcacccagtt cctcctcagc gagttcgtgc caggcgccgg cttcgtgctc    180

ggactagtcc g                                                         191


<210> SEQ ID NO 7
<211> LENGTH: 191
<212> TYPE: DNA
<213> ORGANISM: Artificial Sequence
<220> FEATURE:
<223> OTHER INFORMATION: Description of Artificial Sequence: KB73
      oligonucleotide annealed and extended

<400> SEQUENCE: 7

cggactagtc cgagcacgaa gccggcgcct ggcacgaact cgctgaggag gaactgggtg     60

aggctgaggc tgatgtcgat tggggtgtag ccggtctcga tcctctcgcc gccgagcacc    120

tccacctctg ggttgctgag gcagttgtat gggatgcact cgttgatgtt tgggttgttg    180

tccatggttg t                                                         191
```

-continued

<210> SEQ ID NO 8
<211> LENGTH: 178
<212> TYPE: DNA
<213> ORGANISM: Artificial Sequence
<220> FEATURE:
<223> OTHER INFORMATION: Description of Artificial Sequence: KB72
oligonucleotide extracted with phenol and digested

<400> SEQUENCE: 8
catggacaac aacccaaaca tcaacgagtg catcccatac aactgcctca gcaacccaga 60
ggtggaggtg ctcggcggcg agaggatcga gaccggctac accccaatcg acatcagcct 120
cagcctcacc cagttcctcc tcagcgagtt cgtgccaggc gccggcttcg tgctcgga 178

<210> SEQ ID NO 9
<211> LENGTH: 178
<212> TYPE: DNA
<213> ORGANISM: Artificial Sequence
<220> FEATURE:
<223> OTHER INFORMATION: Description of Artificial Sequence: KB73
oligonucleotide extracted with phenol and digested

<400> SEQUENCE: 9
ctagtccgag cacgaagccg gcgcctggca cgaactcgct gaggaggaac tgggtgaggc 60
tgaggctgat gtcgattggg gtgtagccgg tctcgatcct ctcgccgccg agcacctcca 120
cctctgggtt gctgaggcag ttgtatggga tgcactcgtt gatgtttggg ttgttgtc 178

<210> SEQ ID NO 10
<211> LENGTH: 85
<212> TYPE: DNA
<213> ORGANISM: Artificial Sequence
<220> FEATURE:
<223> OTHER INFORMATION: Description of Artificial Sequence: KB74
oligonucleotide

<400> SEQUENCE: 10
caaggcgccg gcttcgttct cggcctcgtg gacatcatct ggggcatctt cggcccaagc 60
cagtgggacg ccttcccagt gcaga 85

<210> SEQ ID NO 11
<211> LENGTH: 79
<212> TYPE: DNA
<213> ORGANISM: Artificial Sequence
<220> FEATURE:
<223> OTHER INFORMATION: Description of Artificial Sequence: KB75
oligonucleotide

<400> SEQUENCE: 11
cctctagaga tggcctggtt cctggcgaac tcctcgatcc tctggttgat gagctgctcg 60
atctgcactg ggaaggcgt 79

<210> SEQ ID NO 12
<211> LENGTH: 146
<212> TYPE: DNA
<213> ORGANISM: Artificial Sequence
<220> FEATURE:
<223> OTHER INFORMATION: Description of Artificial Sequence: KB74
oligonucleotide annealed and extended

<400> SEQUENCE: 12
caaggcgccg gcttcgttct cggcctcgtg gacatcatct ggggcatctt cggcccaagc 60
cagtgggacg ccttcccagt gcagatcgag cagctcatca accagaggat cgaggagttc 120
gccaggaacc aggccatctc tagagg 146

-continued

<210> SEQ ID NO 13
<211> LENGTH: 146
<212> TYPE: DNA
<213> ORGANISM: Artificial Sequence
<220> FEATURE:
<223> OTHER INFORMATION: Description of Artificial Sequence: KB75 oligonucleotide annealed and extended

<400> SEQUENCE: 13
cctctagaga tggcctggtt cctggcgaac tcctcgatcc tctggttgat gagctgctcg 60
atctgcactg ggaaggcgtc ccactggctt gggccgaaca tgccccagat gatgtccacg 120
aggccgagaa cgaagccggc gccttg 146

<210> SEQ ID NO 14
<211> LENGTH: 135
<212> TYPE: DNA
<213> ORGANISM: Artificial Sequence
<220> FEATURE:
<223> OTHER INFORMATION: Description of Artificial Sequence: KB74 oligonucleotide extracted with phenol and digested

<400> SEQUENCE: 14
gcgccggctt cgttctcggc ctcgtggaca tcatctgggg catcttcggc ccaagccagt 60
gggacgcctt cccagtgcag atcgagcagc tcatcaacca gaggatcgag gagttcgcca 120
ggaaccaggc catct 135

<210> SEQ ID NO 15
<211> LENGTH: 135
<212> TYPE: DNA
<213> ORGANISM: Artificial Sequence
<220> FEATURE:
<223> OTHER INFORMATION: Description of Artificial Sequence: KB75 oligonucleotide extracted with phenol and digested

<400> SEQUENCE: 15
ctagagatgg cctggttcct ggcgaactcc tcgatcctct ggttgatgag ctgctcgatc 60
tgcactggga aggcgtccca ctggcttggg ccgaagatgc cccagatgat gtccacgagg 120
ccgagaacga agccg 135

<210> SEQ ID NO 16
<211> LENGTH: 76
<212> TYPE: DNA
<213> ORGANISM: Artificial Sequence
<220> FEATURE:
<223> OTHER INFORMATION: Description of Artificial Sequence: KB76 oligonucleotide

<400> SEQUENCE: 16
cgtctagact tgagggcctc agcaacctct accagatcta cgccgagagc ttcagggagt 60
gggaggccga cccaac 76

<210> SEQ ID NO 17
<211> LENGTH: 94
<212> TYPE: DNA
<213> ORGANISM: Artificial Sequence
<220> FEATURE:
<223> OTHER INFORMATION: Description of Artificial Sequence: KB77 oligonucleotide

<400> SEQUENCE: 17
ctgggcactg ttcatgtcgt tgaactggat gcgcatctcc tccctgatgg gttggttggg 60

-continued tcggcctccc actcgttggg tcggcctccc actc 94

<210> SEQ ID NO 18
<211> LENGTH: 154
<212> TYPE: DNA
<213> ORGANISM: Artificial Sequence
<220> FEATURE:
<223> OTHER INFORMATION: Description of Artificial Sequence: KB76 oligonucleotide annealed and extended

<400> SEQUENCE: 18
cgtctagact tgagggcctc agcaacctct accagatcta cgccgagagc ttcagggagt 60
gggaggccga cccaacgagt gggaggccga cccaaccaac ccagccctca gggaggagat 120
gcgcatccag ttcaacgaca tgaacagtgc ccag 154

<210> SEQ ID NO 19
<211> LENGTH: 154
<212> TYPE: DNA
<213> ORGANISM: Artificial Sequence
<220> FEATURE:
<223> OTHER INFORMATION: Description of Artificial Sequence: KB77 oligonucleotide annealed and extended

<400> SEQUENCE: 19
ctgggcactg ttcatgtcgt tgaactggat gcgcatctcc tccctgaggg ctgggttggt 60
tgggtcggcc tcccactcgt tgggtcggcc tcccactccc tgaagctctc ggcgtagatc 120
tggtagaggt tgctgaggcc ctcaagtcta gacg 154

<210> SEQ ID NO 20
<211> LENGTH: 148
<212> TYPE: DNA
<213> ORGANISM: Artificial Sequence
<220> FEATURE:
<223> OTHER INFORMATION: Description of Artificial Sequence: KB76 oligonucleotide extracted with phenol and digested

<400> SEQUENCE: 20
ctagacttga gggcctcagc aacctctacc agatctacgc cgagagcttc agggagtggg 60
aggccgaccc aacgagtggg aggccgaccc aaccaaccca gccctcaggg aggagatgcg 120
catccagttc aacgacatga acagtgcc 148

<210> SEQ ID NO 21
<211> LENGTH: 140
<212> TYPE: DNA
<213> ORGANISM: Artificial Sequence
<220> FEATURE:
<223> OTHER INFORMATION: Description of Artificial Sequence: KB77 oligonucleotide extracted with phenol and digested

<400> SEQUENCE: 21
ctgttcatgt cgttgaactg gatgcgcatc tcctccctga gggctgggtt ggttgggtcg 60
gcctcccact cgttgggtcg gcctcccact ccctgaagct ctcggcgtag atctggtaga 120
ggttgctgag gccctcaagt 140